United States Patent
Jones et al.

(10) Patent No.: US 11,761,332 B2
(45) Date of Patent: Sep. 19, 2023

(54) METHODS TO PERFORM AN IN-SITU DETERMINATION OF A FORMATION PROPERTY OF A DOWNHOLE FORMATION AND IN-SITU FORMATION PROPERTY MEASUREMENT TOOLS

(71) Applicant: Halliburton Energy Services, Inc., Houston, TX (US)

(72) Inventors: Christopher Michael Jones, Katy, TX (US); Jonas Toelke, Houston, TX (US); Anthony Herman Van Zulekom, Houston, TX (US); Mehdi Alipour Kallehbasti, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/486,128

(22) PCT Filed: Dec. 4, 2018

(86) PCT No.: PCT/US2018/063917
§ 371 (c)(1),
(2) Date: Aug. 14, 2019

(87) PCT Pub. No.: WO2020/117219
PCT Pub. Date: Jun. 11, 2020

(65) Prior Publication Data
US 2021/0363883 A1    Nov. 25, 2021

(51) Int. Cl.
*E21B 49/08*    (2006.01)
*E21B 43/12*    (2006.01)
(Continued)

(52) U.S. Cl.
CPC ............ *E21B 49/088* (2013.01); *E21B 43/12* (2013.01); *E21B 49/008* (2013.01); *G01N 33/2823* (2013.01)

(58) Field of Classification Search
CPC ...... E21B 49/088; E21B 43/12; E21B 49/008; G01N 33/2823
See application file for complete search history.

(56) References Cited

U.S. PATENT DOCUMENTS 5,335,542 A * 8/1994 Ramakrishnan .... E21B 33/1246
166/250.02
6,061,634 A * 5/2000 Belani ................... E21B 49/008
702/12

(Continued)

OTHER PUBLICATIONS

International Search Report and Written Opinion in PCT/US2018/063917, dated Aug. 23, 2019.

*Primary Examiner* — Nicole Coy
(74) *Attorney, Agent, or Firm* — Barnes & Thornburg LLP

(57) ABSTRACT

The disclosed embodiments include methods to perform an in-situ determination of a formation property of a downhole formation, methods to operate a tool to perform an in-situ determination of formation properties of a downhole formation, and in-situ formation property measurement tools. In one embodiment, a method to perform an in-situ determination of a formation property includes deploying a tool into a borehole that is drilled through a formation. The method also includes isolating a source zone from an injection zone. While the source zone is isolated from the injection zone, the method further includes withdrawing a fluid that partially fills the source zone; flowing the fluid into the injection zone; injecting the fluid into a first portion of the formation that is along the injection zone; and determining at least one formation property of the first portion based on an injection of the fluid into the first portion.

20 Claims, 6 Drawing Sheets

(51) Int. Cl.
*E21B 49/00* (2006.01)
*G01N 33/28* (2006.01)

(56) References Cited

U.S. PATENT DOCUMENTS

| | | |
|---|---|---|
| 7,963,327 B1 | 6/2011 | Saleri et al. |
| 7,999,542 B2 | 8/2011 | Ramamoorthy et al. |
| 8,191,416 B2 | 6/2012 | Kuchuk et al. |
| 8,297,354 B2 | 10/2012 | Ayan et al. |
| 8,720,552 B2 | 5/2014 | Ayan et al. |
| 9,051,822 B2 * | 6/2015 | Ayan ................ E21B 43/25 |
| 9,371,710 B2 | 6/2016 | Ramakrishnan et al. |
| 2002/0017387 A1 | 2/2002 | Ringgenberg et al. |
| 2003/0226663 A1 | 12/2003 | Krueger et al. |
| 2009/0255669 A1 | 10/2009 | Ayan et al. |
| 2010/0126717 A1 | 5/2010 | Kuchuk et al. |
| 2010/0264915 A1 | 10/2010 | Saldungaray et al. |
| 2010/0277166 A1 | 11/2010 | Ramamoorthy et al. |
| 2011/0061863 A1 | 3/2011 | Ramakrishnan et al. |
| 2011/0198078 A1 | 8/2011 | Harrigan et al. |
| 2012/0024523 A1 | 2/2012 | Ayan et al. |

\* cited by examiner

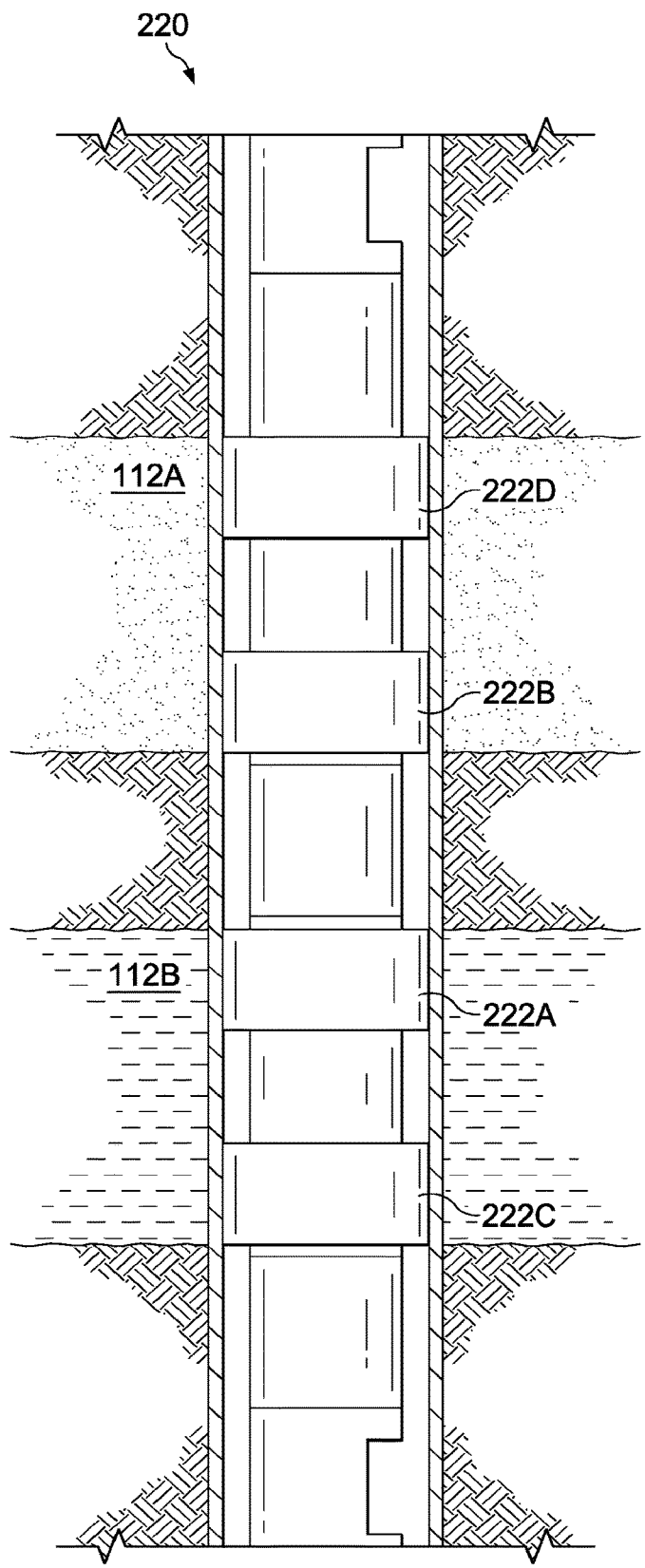
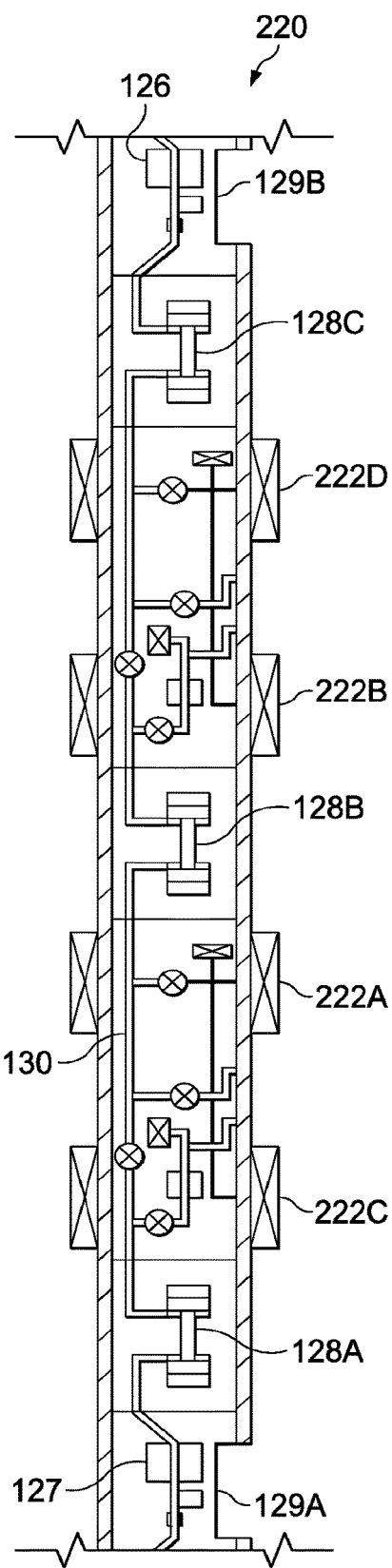
FIG. 2C
FIG. 2D

METHODS TO PERFORM AN IN-SITU DETERMINATION OF A FORMATION PROPERTY OF A DOWNHOLE FORMATION AND IN-SITU FORMATION PROPERTY MEASUREMENT TOOLS

BACKGROUND

The present disclosure relates generally to methods to perform an in-situ determination of a formation property of a downhole formation, methods to operate a downhole tool to perform an in-situ determination of one or more formation properties of a downhole formation, and in-situ formation property measurement tools.

Water flood enhanced oil recovery methods are sometimes designed based on modeling of existing production wells in combination with extensive laboratory testing with formation cores, which are excavated from a downhole formation. However, while the excavated cores are being transported from a native downhole environment to the surface, and eventually to a laboratory facility, the cores often experience atmospheric pressure, or may be contaminated by containments, thereby damaging the cores, and rendering testing less reliable or unreliable. Further, performing surface-based testing is often time consuming and labor intensive, thereby adversely impacting hydrocarbon production and exploration.

BRIEF DESCRIPTION OF THE DRAWINGS

Illustrative embodiments of the present disclosure are described in detail below with reference to the attached drawing figures, which are incorporated by reference herein, and wherein:

FIG. 2C is a schematic, perspective view of another in-situ formation property measurement tool similar to the in-situ formation property measurement tool of FIGS. 2A and 2B, after the in-situ formation property measurement tool has isolated a source zone of the borehole from an injection zone of the borehole;

FIG. 2D is a schematic, cross-sectional view of the in-situ formation property measurement tool of FIG. 2C;

Figure 1A:
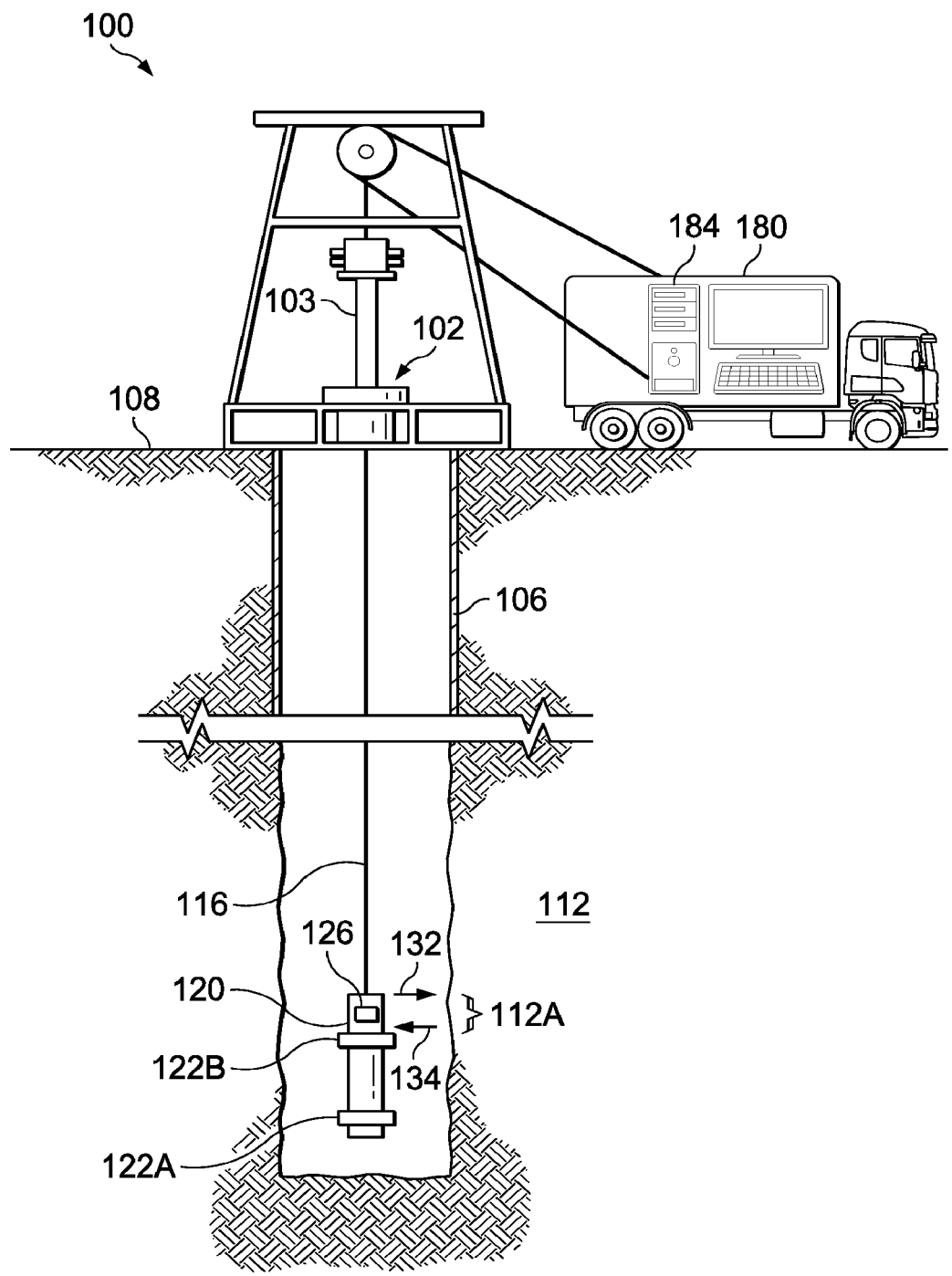
FIG. 1A is a schematic, side view of a wireline environment with an in-situ formation property measurement tool deployed in a borehole to perform an in-situ determination of formation properties of a downhole formation.

The illustrated figures are only exemplary and are not intended to assert or imply any limitation with regard to the environment, architecture, design, or process in which different embodiments may be implemented.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

The present disclosure relates to methods to perform an in-situ determination of a formation property of a downhole formation, methods to operate a downhole tool to perform an in-situ determination of one or more formation properties of a downhole formation, and in-situ formation property measurement tools. The method includes deploying a downhole tool into a borehole that is drilled through a formation. In some embodiments, the downhole tool is an in-situ formation property measurement tool illustrated in FIGS. 1A-1B and 2A-2B. Additional descriptions of the in-situ formation property measurement tool are provided in the paragraphs below. Once the downhole tool has been deployed at a desired location, the borehole is sealed to form a source zone and an injection zone that are isolated from each other. As referred to herein, a source zone defines a zone that is partially or completely filled with an injection fluid that is extracted and injected into an injection zone. Further, and as referred to herein, an injection zone defines a zone that is partially or completely filled with the injection fluid before the injection fluid is injected into the formation. For example, in the depicted embodiment of FIG. 2A, the source zone is a water-bearing zone whereas the injection zone in an oil-bearing zone. Further, and as referred to herein, an injection fluid refers to a fluid or mixture that is injected into the formation.

In some embodiments, the injection fluid is a formation fluid extracted from a reservoir. In some embodiments, the injection fluid is petroleum extracted from a hydrocarbon reservoir. In one or more of the foregoing embodiments, the formation fluid or petroleum is extracted from the formation before the borehole is sealed by the foregoing process. In other embodiments, the source zone and the injection zone of the borehole are first sealed, and the formation fluid or petroleum is extracted from the formation after the completion of the sealing process. In some embodiments, the injection fluid is a drilling fluid or another type of fluid or mixture that is pumped downhole.

In some embodiments, where the borehole is partially filled with two types of fluids (e.g., at least one component of formation fluids, at least one component of drilling fluids, at least one component of petroleum, mud mixtures, as well as other types of fluids), the borehole is sealed such that neither the source nor the injection zone reside in a transition zone between the two fluids. For example, where the borehole is filled with water and petroleum, and petroleum flows above water, a transition zone is a zone where fluids within the zone contain a mixture of petroleum and water. In one exemplary embodiment, the injection zone is a petroleum-bearing zone containing petroleum, whereas the source zone is a water-bearing zone containing water. In a second and alternative embodiment, the source zone is the petroleum-bearing zone and the injection zone is the water-bearing zone.

Once the source zone and the injection zone of the borehole have been isolated from each other, and while the source zone of the borehole is partially or completely filled with an injection fluid that is extracted from the formation or pumped downhole, the injection fluid is withdrawn from the source zone and pumped into the injection zone. In some embodiments, where the in-situ formation property measurement tool illustrated in FIGS. 1A-1B and 2A-2B is deployed, a pump of the in-situ formation property measurement tool pumps the injection fluid from the source zone through an internal annulus of the in-situ formation property measurement tool, and out to the injection zone. In one or more of such embodiments, the internal annulus forms a fluid flow path from a first portion of the tool that is deployed in the source zone of the borehole to a second portion of the tool that is deployed in the injection zone of the borehole. The injection fluid is then injected into a portion of the formation that is deposited along the injection zone of the borehole. In some embodiments, the portion of the formation is a section of formation rock being injected or targeted to be injected with the injected fluid extracted from the first portion. In some embodiments, the injection fluid is treated with an additive (while the injection fluid is in the source zone, while the injection fluid is flowing through the annulus, or after the injection fluid has been injected into the injection zone) to improve the injectability of the injection fluid. In one or more of such embodiments, chemical property modifiers and/or physical property modifiers, such as viscosifiers, scale inhibitors, asphaltene inhibitors, oil wetting agents, water wetting agents, biocides, and sulfur compound treating agents, are added to modify the downhole fluid properties to better match the properties of fluids for which an enhanced oil recovery is to be designed. In some embodiments, properties of fluids injected into the formation are modified as to prevent formation damage. In one or more embodiments, such modifications are targeted if the injection fluids, production fluids, and/or formation properties are analyzed in-situ. In one or more embodiments, such analysis is accomplished with formation tester sensors such as resistivity sensors, capacitance sensors, PVT apparatus such as a fluid expansion or compression piston, optical sensors, chromatography sensors such as liquid chromatography or gas chromatography, electrochemistry sensors, colorimetry indicator sensors, thermal physical property sensors, viscosity sensors, or mass spectrometry sensors. In some embodiments, a microfluidic apparatus is used to perform wet chemistry measurement techniques, which utilize the mixing of chemicals and chemical reagents to derive chemical and/or physical property information.

In some embodiments, a fluid compatibility of the injection fluid is tested by mixing the injection fluid with a test fluid. In one or more of such embodiments, the test fluid is withdrawn from the source zone. In some embodiments, the fluid compatibility of the injection fluid is inferred by monitoring pressure buildup and dissipation with respect to injection rate. For example, if the pressure increases significantly over time during injection, a degree of lack of compatibility between the injection fluid and the formation may be inferred. In some embodiments, the injection fluid is modified, and further tests are conducted to test the compatibility of the modified injection fluid. In one or more embodiments, materials carried downhole in a sample apparatus are mixed with the injection fluid to modify the injection fluid and to improve the compatibility of the injection fluid. In one or more embodiments, two separate pumps joining the injection fluid and another fluid from two streams into one stream are utilized to mix the injection fluid with another fluid. In one or more embodiments, the fluids are mixed at the inlet to the wellbore formation zone. In one or more embodiments, the foregoing mixing operation utilizes a dual port oval pad or a dual port straddle packer. In one or more embodiments, the foregoing mixing operation combines a wellbore drilling fluid filtrate with a source zone formation fluid to modify viscosity, density, or ionic strength (salinity) of the mixture prior to injecting the mixture into the formation.

One or more measurements (e.g., by sensors or probes of the in-situ formation property measurement tool or by other downhole sensors/probes) of the injection fluid being injected into the first portion of the formation are made. Examples of sensors used to measure formation properties include, but are not limited to, electromagnetic sensors, acoustic sensors, nuclear sensors, NMR sensors, and image sensors. Further, a determination of one or more formation properties of the first portion of the formation is made based on the measurements obtained by the sensors or probes. For example, the formation permeability of the first portion of the formation may be determined based on the fluid viscosity of the injection fluid that is injected into the first portion of the formation. Examples of formation properties include, but are not limited to, the mobility, relative permeability of the first portion of the formation, the fluid injection potential of the first portion of the formation, the wettability of the first portion of the formation, the formation pressure of the first portion of the formation, the mobility anisotropy of the first portion of the formation, as well as other types of formation properties for projecting enhanced oil recovery. In some embodiments, such properties are determined by withdrawing and/or injection fluids from or into the formation in accordance with one or more processes described herein. In some embodiments, properties of the injection fluid (e.g., the flow rate of the injection fluid, the pressure of the injection fluid, the density of the injection fluid, viscosity of the injection fluid, etc.) being injected into the first portion of the formation are measured and the properties of the first portion formation are determined based on the properties of the injection fluid. In one or more embodiments, such fluid properties are measured, assumed, or estimated. In some embodiments, assumptions of the fluid properties are made based on properties of offset wells, and estimations are made based on state or thermodynamic chemical property models. In one or more embodiments, fluid properties are determined based on a combination of measurements, assumptions, or estimations.

In some embodiments, proxy fluids are analyzed in a laboratory utilizing fluids obtained from either downhole sampling or surface sampling. In some embodiments, proxy formation properties are also analyzed in a laboratory with proxy samples obtained from offset wells or samples from formations of similar type. In some embodiments, such samples (e.g., core samples) are obtained by drill cutting the formation. In some embodiments, a combination of the foregoing in-situ and surface-based operations are performed to determine the formation properties of the formation.

In some embodiments, the injected fluid facilitates hydrocarbon recovery. In one or more embodiments, after the injection fluid is injected into the first portion of the formation, petroleum deposited in a hydrocarbon reservoir or a mixture of petroleum and the injected fluid (mixture) also flows from the hydrocarbon deposit, out of the first portion of the formation, and into the injection zone. In one or more of such embodiments, properties of petroleum or the mixture (e.g., the flow rate of petroleum or the mixture, the pressure of petroleum or the mixture, the density of petroleum or the mixture, viscosity of petroleum or the mixture, etc.) are also measured. In one or more of such embodiments, the properties of petroleum or the mixture are used to determine the formation properties of the formation. In one or more embodiments, the foregoing described measurements are measured over time and the formation properties of the formation are determined over a desired period of time (e.g., hour, day, week, or another period of time). Additional descriptions of methods to perform an in-situ determination of a formation property of a downhole formation, methods to operate a downhole tool to perform an in-situ determination of one or more formation properties of a downhole formation, and in-situ formation property measurement tools are described in the paragraphs below and are illustrated in FIGS. 1-4.

Turning now to the figures, FIG. 1A is a schematic, side view of a wireline environment 100 with an in-situ formation property measurement tool 120 deployed in a borehole 106 to perform an in-situ determination of formation properties of a downhole formation 112. FIG. 1A may also represent another completion or preparation environment where a logging operation is performed. In the embodiment of FIG. 1A, a well 102 having the borehole 106 extends from a surface 108 of the well 102 to or through a formation 112. A conveyance 116, optionally carried by a vehicle 180, is positioned proximate to the well 102. The conveyance 116, along with the in-situ formation property measurement tool 120 are lowered down the borehole 106, i.e. downhole.

In one or more embodiments, the conveyance 116 and the in-situ formation property measurement tool 120 are lowered downhole through a blowout preventer 103. In one or more embodiments, the conveyance 116 may be wireline, slickline, coiled tubing, drill pipe, production tubing, fiber optic cable, downhole tractor or another type of conveyance operable to deploy the in-situ formation property measurement tool 120. The conveyance 116 provides mechanical suspension of the in-situ formation property measurement tool 120 as the in-situ formation property measurement tool 120 is deployed downhole. In one or more embodiments, the conveyance 116 also transmits signals including, but not limited to, optical signals to the in-situ formation property measurement tool 120. In one or more embodiments, the conveyance 116 also provides power to the in-situ formation property measurement tool 120 as well as other downhole components. In one or more embodiments, the conveyance 116 also provides downhole telemetry. Additional descriptions of telemetry are provided in the paragraphs below. In one or more embodiments, the conveyance 116 also provides a combination of power and downhole telemetry to the in-situ formation property measurement tool 120. For example, where the conveyance 116 is a wireline, coiled tubing (including electro-coiled-tubing), or drill pipe, power and data are transmitted along the conveyance 116 to the in-situ formation property measurement tool 120.

In the illustrated embodiment of FIG. 1A, the in-situ formation property measurement tool 120 includes a first set of formation testing probes 122A, a second set of formation testing probes 122B, and a sensor 126. As referred to herein, a formation testing probe is any device that seals the borehole to form isolation zones along one or more sections of the borehole. In some embodiments, the first and second sets of formation testing probes 122A and 122B, respectively, are packers coupled to the in-situ formation property measurement tool 120. In one or more embodiments, the first and second sets of formation testing probes 122A and 122B, respectively, are pads and are deployed from the in-situ formation property measurement tool 120. Further, although the depicted embodiment of FIG. 1A illustrates each set of formation testing probes having two formation testing probes, in other embodiments, one or more sets of the formation testing probes of the in-situ formation property measurement tool 120 include a different number of formation testing probes. In the depicted embodiment of FIG. 1A, once the in-situ formation property measurement tool 120 is deployed at a desired location, the packers expand to seal off a borehole, such as the borehole 106 of FIG. 1A and to form the desired zones such as a source zone and an injection zone of the borehole 106 of FIG. 1A. The in-situ formation property measurement tool 120 also includes one or more pumps (shown in FIGS. 2A and 2B) and an internal annulus (shown in FIG. 2B) that provides a fluid flow path for fluids to flow through the in-situ formation property measurement tool 120.

In some embodiments, the in-situ formation property measurement tool 120, after forming the source zone and the injection zone, actuates the one or more pumps to withdraw injection fluid that fills or partially fills the source zone, pumps the injection fluid through the internal annulus into the injection zone, and injects the injection fluid into a first portion of the formation 112A. In the illustrated embodiment of FIG. 1A, the in-situ formation property measurement tool 120 includes sensor 126, which is operable of measuring one or more fluid properties (e.g., the flow rate of the injection fluid, the pressure of the injection fluid, the density of the injection fluid, viscosity of the injection fluid, etc.) of the injection fluid as the injection fluid is injected into the first portion of the formation 112A (e.g., in a direction indicated by arrow 132). In one or more embodiments, where petroleum of a hydrocarbon reservoir deposited in the formation 112 or a mixture of petroleum and the injected fluid (mixture) flows out from the first portion of the formation 112A (e.g., in a direction indicated by arrow 134), the sensor 126 is also operable of measuring one or more properties of petroleum or the mixture. Examples of the measured properties, include, but are not limited to, the flow rate of petroleum or the mixture, the pressure of petroleum or the mixture, the density of petroleum or the mixture, viscosity of petroleum or the mixture, compressibility, bubble point, capacitance, resistivity, thermos-physical properties, chemical properties of petroleum such as, but not limited to, composition, pH, salinity, ionic strength, cation exchange capacity, saturates, aromatics, resins, asphaltenes (SARA) fractions, as well as other measureable properties of petroleum. In one or more embodiments, where the hydrocarbon reservoir is deposited near the first portion of the formation 112A, reservoir properties of the hydrocarbon reservoir are determined based on the properties of the injection fluid, a mixture of the injection fluid and petroleum, and/or petroleum. Similarly, where another type of reservoir is deposited near the first portion of the formation 112A, reservoir properties of the nearby reservoir are determined based on the properties of the injection fluid, a mixture of the injection fluid and the reservoir fluid, and/or the reservoir fluid.

In some embodiments, the in-situ formation property measurement tool 120 includes a processor unit and memory (not shown). In one or more of such embodiments, the processor unit executes instructions stored in the memory to determine formation properties (e.g., the relative permeability of the first portion of the formation 112A, the fluid injection potential of the first portion of the formation 112A, the wettability of the first portion of the formation 112A, as well as other types of formation properties for projecting enhanced oil recovery) of the first portion of the formation 112A. In one or more embodiments, the processor unit also determines the formation properties of the first portion of the formation 112A over time. In one or more embodiments, the processor unit also generates one or more enhanced oil recovery models based on the obtained measurements of fluids flowing through the first portion of the formation 112A as well as the formation properties of the first portion of the formation 112A.

In some embodiments, the in-situ formation property measurement tool 120 is communicatively connected to the controller 184 via a telemetry system described herein and is operable to transmit data indicative of measurements obtained by the sensor 126 to the controller 184. In one or more embodiments, where the in-situ formation property measurement tool 120 also includes a processor unit and a memory, the in-situ formation property measurement tool 120 is also operable to transmit data indicative of formation properties of the first portion of the formation 112A as well as enhanced oil recovery models via the telemetry system to the controller 184. An operator may then access the controller 184 to analyze such data. As defined herein, the controller 184 represents any electronic device operable to receive data indicative of measurements made by the sensor 126 or by other sensors (such as sensor 127 of FIG. 2B) of the in-situ formation property measurement tool 120. In one or more embodiments, a processor of the controller 184, after receiving data indicative of measurements made by the sensor 126, determines the formation properties of the first portion of the formation 112A and provides the formation properties for display for the operator to analyze.

Figure 1B:
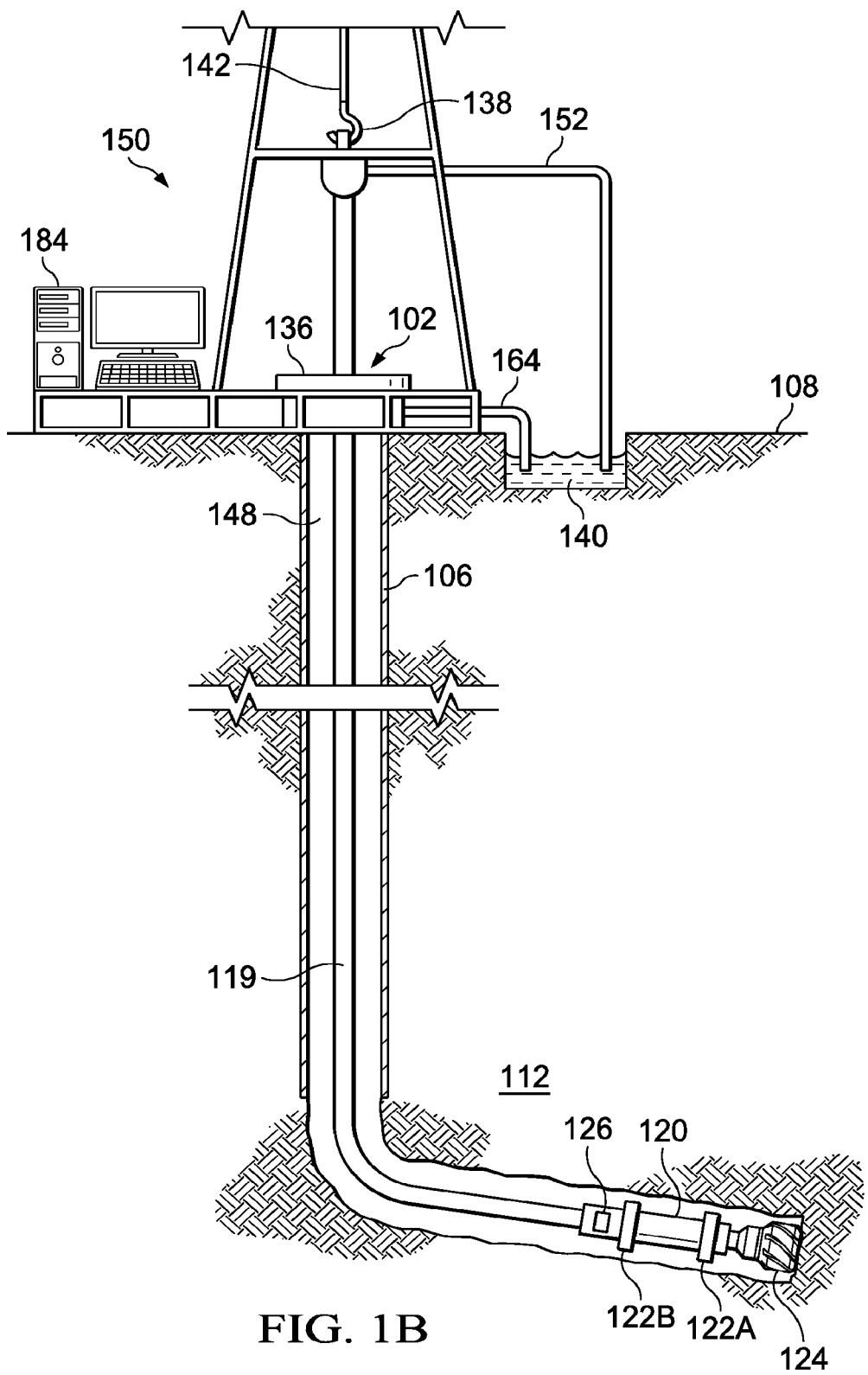
FIG. 1B is a schematic, side view of a logging while drilling (LWD)/measurement while drilling (MWD) environment with the in-situ formation property measurement tool of FIG. 1A deployed in a borehole to perform an in-situ determination of formation properties of a downhole formation.

FIG. 1B is a schematic, side view of a logging while drilling (LWD)/measurement while drilling (MWD) environment 150 with the in-situ formation property measurement tool 120 of FIG. 1A deployed in a borehole to perform an in-situ determination of formation properties of the downhole formation 112. FIG. 1B may also represent another completion or preparation environment where a drilling operation is performed. A hook 138, cable 142, traveling block (not shown), and hoist (not shown) are provided to lower a drill sting 119 down the borehole 106 or to lift the drill string 119 up from the borehole 106.

At the wellhead 136, an inlet conduit 152 is coupled to a fluid source (not shown) to provide fluids, such as drilling fluids, downhole. The drill string 119 has an internal cavity that provides a fluid flow path from the surface 108 down to the in-situ formation property measurement tool 120. In some embodiments, the fluids travel down the drill string 119, through the in-situ formation property measurement tool 120, and exit the drill string 119 at the drill bit 124. The fluids flow back towards the surface 108 through a wellbore annulus 148 and exit the wellbore annulus 148 via an outlet conduit 164 where the fluids are captured in container 140. In LWD systems, sensors or transducers (not shown) are typically located at the lower end of the drill string 119. In one or more embodiments, sensors employed in LWD applications are built into a cylindrical drill collar that is positioned close to the drill bit 124. While drilling is in progress, these sensors continuously or intermittently monitor predetermined drilling parameters and formation data, and transmit the information to a surface detector by one or more telemetry techniques, including, but not limited to, mud pulse telemetry, acoustic telemetry, and electromagnetic wave telemetry. In one or more embodiments, where a mud pulse telemetry system is deployed in the borehole 106 to provide telemetry, telemetry information is transmitted by adjusting the timing or frequency of viable pressure pulses in the drilling fluid that is circulated through the drill string 119 during drilling operations. In one or more embodiments, an acoustic telemetry system that transmits data via vibrations in the tubing wall of the drill string 119 is deployed in the borehole 106 to provide telemetry. More particularly, the vibrations are generated by an acoustic transmitter (not shown) mounted on the drill string 119 and propagate along the drill string 119 to an acoustic receiver (not shown) also mounted on the drill string 119. In one or more embodiments, an electromagnetic wave telemetry system that transmits data using current flows induced in the drill string 119 is deployed in the borehole 106 to provide telemetry. Additional types of telemetry systems, such as electric telemetry or optical telemetry, may also be deployed in the borehole 106 to transmit data from the in-situ formation property measurement tool 120 and other downhole components to the controller 184.

In some embodiments, the in-situ formation property measurement tool 120 of FIGS. 1A and 1B (or another downhole tool (not shown)) obtains a sample of the injection fluid, transports the sample fluid to a surface-based laboratory (not shown), where measurements of the fluid properties of the injection fluid are obtained in the laboratory. Additional descriptions of the operations performed by the in-situ formation property measurement tool 120 are provided in the paragraphs below. Although FIGS. 1A and 1B each illustrates a single in-situ formation property measurement tool 120 deployed in the borehole 106, multiple in-situ formation property measurement tools may be simultaneously deployed in the borehole 106 to perform operations described herein. For example, a second in-situ formation property measurement tool (not shown) may be deployed in another section of the borehole 106 to isolate two zones (not shown), withdraw a second fluid (second injection fluid) that fills or partially fills one of the zones, and inject the second injection fluid into another portion of the formation 112. In one or more of such embodiments, the second injection fluid and the first injection fluid are the same type of fluid. In one or more embodiments, the first and second injection fluids are different types of fluids (e.g., the first type of injection fluid is water, whereas the second type of injection fluid is petroleum). Further, although the in-situ formation property measurement tool 120 of FIGS. 1A and 1B includes two formation testing probes 122A and 122B, in other embodiments, the in-situ formation property measurement tool 120 includes a different number of formation testing probes that are operable to form a different number of isolated zones. For example, the in-situ formation property measurement tool 120 may include a third formation testing probe (not shown) and a fourth formation testing probe (not shown) that are deployable to form a third zone and a fourth zone. The in-situ formation property measurement tool 120 is further operable to withdraw fluid that fills or partially fills one of the third or fourth zones, pump the injection fluid into the other zone, inject the injection fluid into another portion of the formation, measure fluid properties of the injected fluid, and determine formation properties of the other portion of the formation. Although the depicted embodiments of FIGS. 1A and 1B illustrate one sensor 126, in some embodiments, multiple sensors are deployed on the measurement tool 120 to perform operations performed by the sensor 126. In some embodiments, the sensor 126 as illustrated in FIGS. 1A and 1B represents multiple sensors operating together to perform the operations described herein.

Figure 2A:
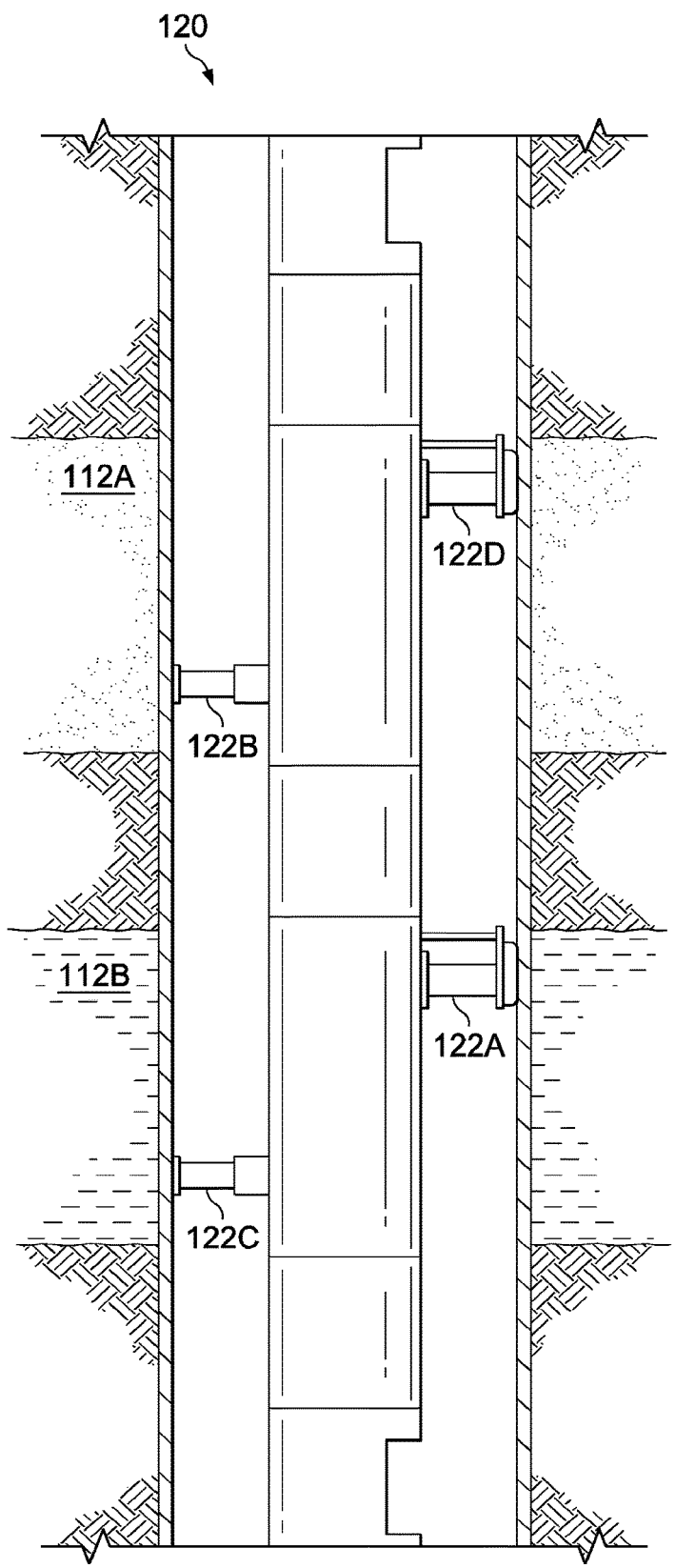
FIG. 2A is a schematic, perspective view of the in-situ formation property measurement tool of FIG. 1A, after the in-situ formation property measurement tool has isolated a source zone of the borehole from an injection zone of the borehole.
Figure 2B:
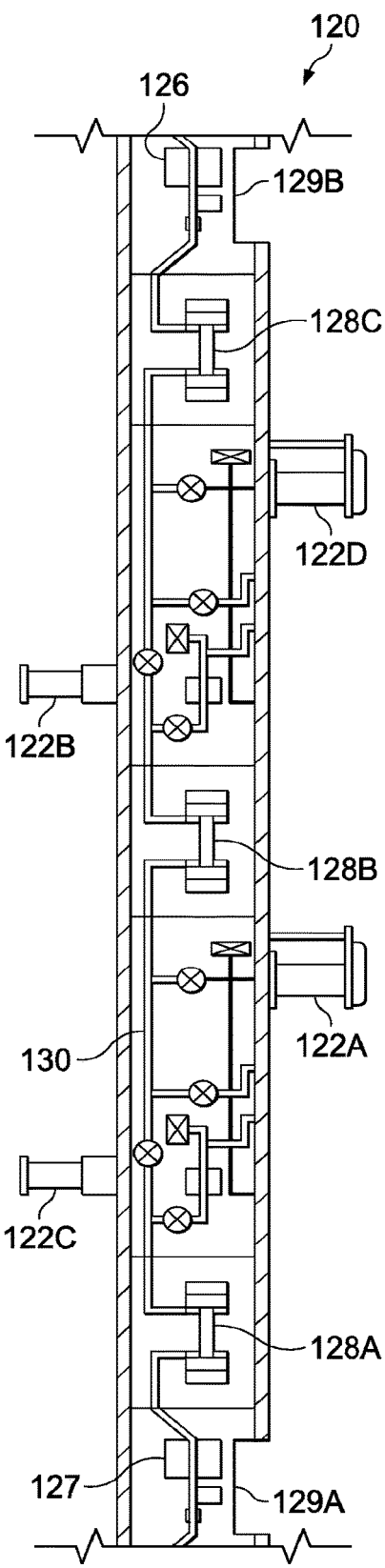
FIG. 2B is a schematic, cross-sectional view of the in-situ formation property measurement tool of FIG. 2A.

FIG. 2A is a schematic, perspective view of the in-situ formation property measurement tool 120 of FIG. 1A, after the in-situ formation property measurement tool 120 has isolated a source zone of the borehole from an injection zone of the borehole. In the illustrated embodiment of FIG. 2A, the source zone is a water-bearing zone and is formed after a first set of formation testing probes 122A and 122C are deployed. Further, the first portion of the formation 112A is a section of the formation 112 that is in the petroleum-bearing zone, whereas a second portion of the formation 112B is another section of the formation 112 that is in the water-bearing zone. FIG. 2B is a schematic, cross-sectional view of the in-situ formation property measurement tool 120 of FIG. 2A. In the illustrated embodiment, the in-situ formation property measurement tool 120 includes a first aperture 129A that allows fluids to flow from the water-bearing zone into the in-situ formation property measurement tool 120 or from the in-situ formation property measurement tool 120 into the water-bearing zone. Similarly, the in-situ formation property measurement tool 120 also includes a second aperture 129B that allows fluids to flow from the petroleum-bearing zone into the in-situ formation property measurement tool 120 or from the in-situ formation property measurement tool 120 out to the petroleum-bearing zone. In one or more embodiments, the in-situ formation property measurement tool 120 is operable of selectively opening or closing the first and second apertures 129A and 129B to control fluid flow. In the illustrated embodiment, the injection fluid is water. Further, the in-situ formation property measurement tool 120 includes a first pump 128A that is operable of pumping water from the water-bearing zone into an internal annulus 130 of the in-situ formation property measurement tool 120. In the illustrated embodiment of FIG. 2B, the internal annulus forms a fluid flow path that connects a portion of the in-situ formation property measurement tool 120 that is deployed in the water-bearing zone with another portion of the in-situ formation property measurement tool 120 that is deployed in the petroleum-bearing zone. The second pump 128B and the third pump 128C facilitate pumping water along the internal annulus 130 and injecting water flowing through the internal annulus 130 into the petroleum-bearing zone.

The in-situ formation property measurement tool 120 also includes sensor 126, which is operable of measuring fluid properties of water or other fluids flowing through the internal annulus 130. Further, the sensor 127 is also operable of measuring fluid properties of the water being injected into the first portion of the formation 112A. In some embodiments, the in-situ formation property measurement tool 120 also includes a fluid injection device (not shown) that is deployed in the petroleum-bearing zone and operable to inject water into the first portion of the formation 112A. In some embodiments, where petroleum or other types of fluids or mixtures flow out of the first portion of the formation 112A, the sensor 126 is also operable of measuring the fluid properties of petroleum or other types of fluids or mixtures that flow out of the first portion of the formation 112A.

In some embodiments, the in-situ formation property measurement tool 120 is also operable of performing reverse injection operations. In one or more embodiments, the in-situ formation property measurement tool 120 is operable of pumping petroleum (which in this embodiment is also an injection fluid) from the petroleum-bearing zone, through the second aperture 129B, along the internal annulus 130, and into the water-bearing zone. In such embodiments, the sensor 127 is operable of measuring fluid properties of petroleum or other fluids flowing through the internal annulus 130. Further, the sensor 127 is also operable of measuring fluid properties of petroleum (or other fluids) being injected into a second portion of the formation 112B. In some embodiments, the in-situ formation property measurement tool 120 also includes a fluid injection device (not shown) that is deployed in the water-bearing zone and operable to inject petroleum (or other fluids) into the second portion of the formation 112B. In some embodiments, where petroleum or other types of fluids or mixtures flow out of the second portion of the formation 112B, the sensor 126 is also operable of measuring the fluid properties of petroleum or other types of fluids or mixtures that flow out of the second portion of the formation 112B. In some embodiments, the in-situ formation property measurement tool 120 includes additional sensors (not shown) that are deployed a further distance from the first portion of the formation 112A relative to the distance from the sensor 126. In one or more of such embodiments, the additional sensors are operable of measuring a pulse of water (or another type of fluid) as water (or another type of fluid) is injected into the first portion of the formation 112A. Similarly, the additional sensors are also operable of measuring a pulse of petroleum (or another fluid) flowing out of the first portion of the formation 112A.

In some embodiments, the in-situ formation property measurement tool 120 includes a tool (e.g., drill) operable to perform a drill cutting operation to obtain a sample core of the first portion of the formation 112A. In one or more of such embodiments, the in-situ formation property measurement tool 120 or another tool deployed in the borehole 106 is operable of transporting the sample core to the surface, where the sample core is analyzed to determine the formation properties of the first portion of the formation 112A. The foregoing operation and analysis may be performed before the injection fluid is injected into the first portion of the formation 112A. In one or more of such embodiments, formation properties of the first portion of the formation 112A are first determined, and the injection rate at which the injection fluid is injected into the first portion of the formation 112A is based on the determined formation properties of the first portion of the formation 112A.

FIGS. 2C and 2D respectively illustrate a schematic, perspective view and a schematic cross-sectional view of another in-situ formation property measurement tool 220 that is similar to the in-situ formation property measurement tool 120 of FIGS. 2A and 2B. In the illustrated embodiments of FIGS. 2C and 2D, the in-situ formation property measurement tool 220 has isolated a source zone of the borehole 106 from an injection zone of the borehole 106. In the illustrated embodiments of FIGS. 2C and 2D, packers 222A, 222B, 222C, and 222D are deployed in lieu of probes 122A, 122B, 122C, and 122D to isolate the first portion of the formation 112A and the second portion of the formation 122B. Although FIGS. 2A-2D illustrate deployment of probes 122A-122D and packers 222A-222D, the in-situ formation property measurement tools 120 and 220 of FIGS. 2A-2D are operable of deploying a variety of other devices to isolate one or more zones of the borehole.

Although FIGS. 2A and 2C illustrate a water-bearing zone and a petroleum-bearing zone, other types of zones that are filled with other types of fluids may be formed by deploying the formation testing probes 122A-122D. Further, although the embodiment of FIGS. 2B and 2D illustrate three pumps, 128A-128C, in other embodiments, the in-situ formation property measurement tools 120 and 220 include a different number of pumps to facilitate fluid flow through the internal annulus 130.

Figure 3:
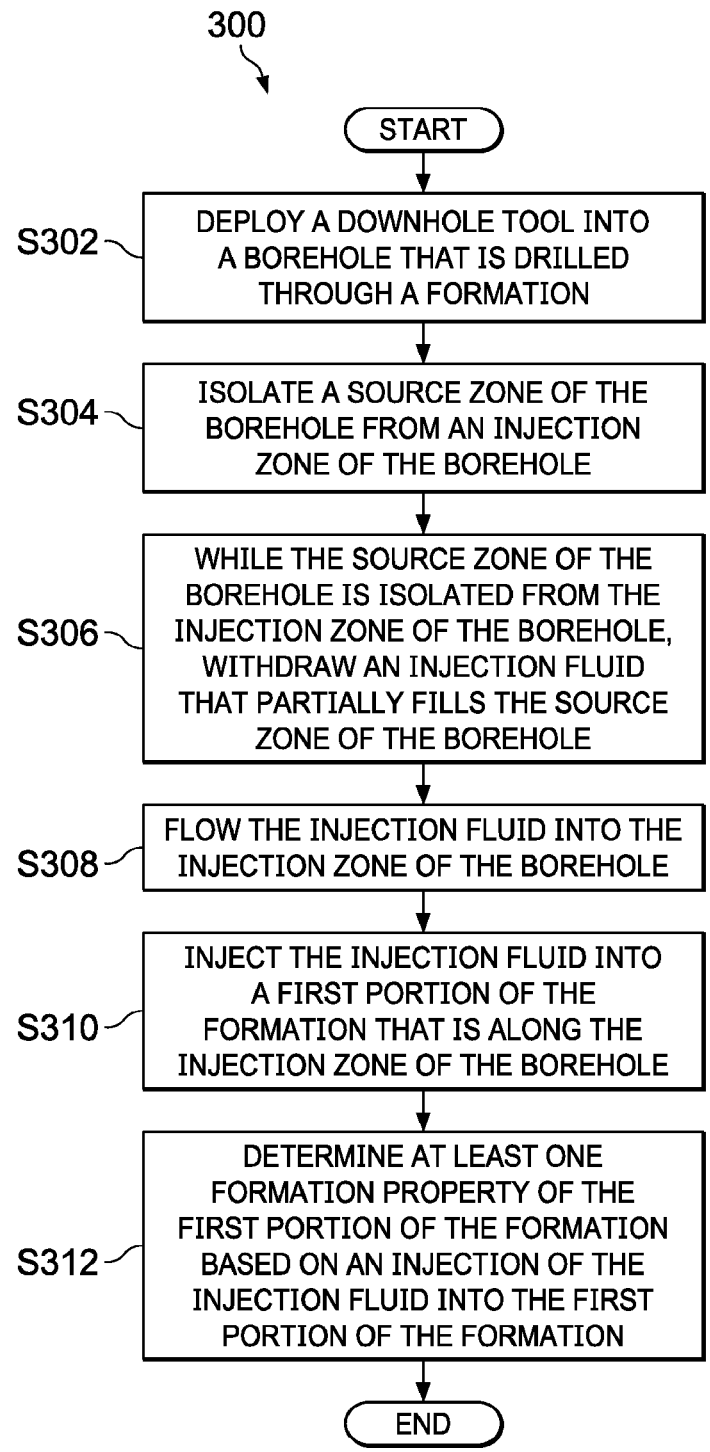
FIG. 3 is a flow chart of a process to perform an in-situ determination of formation properties of a downhole formation.

FIG. 3 is a flow chart of a process 300 to perform an in-situ determination of formation properties of a downhole formation. Although the operations in the process 300 are shown in a particular sequence, certain operations may be performed in different sequences or at the same time where feasible.

At block S302, a downhole tool, such as the in-situ formation property measurement tool 120 of FIGS. 1A-1B and 2A-2B, is deployed into a borehole that is drilled through a formation. At block S304, a source zone of the borehole is isolated from an injection zone of the borehole. In the embodiment of FIG. 2A, the first and second sets of formation testing probes 122A and 112C, and 122B and 112D, respectively, are deployed from the in-situ formation property measurement tool 120 to seal the borehole 106 and to form a water-bearing zone and a petroleum-bearing zone. In some embodiments, additional formation testing probes are deployed to isolate other zones from each other. Although the embodiment of FIG. 2A illustrates the source zone as a water-bearing zone, in some embodiments, the source zone is filled with other types of fluids such as, but not limited to, formation fluids, petroleum, drilling fluids, as well as other types of fluids. In one or more embodiments, fluid (e.g., drilling fluid, mud/mixture, water, etc.) is pumped from the surface to fill or partially fill the source zone.

At block S306, and while the source zone of the borehole is isolated from the injection zone of the borehole, an injection fluid that partially fills the source zone of the borehole is withdrawn. In the embodiment of FIGS. 2A and 2B, where water partially fills the source zone, water flows from the source zone, through the aperture 129A, and into the internal annulus 130 of the in-situ formation property measurement tool 120. In one or more embodiments, where the source zone is filled or partially filled with another type of injection fluid, the other type of injection fluid is pumped into the in-situ formation property measurement tool 120.

At block S308, the injection fluid flows into the injection zone of the borehole. In the illustrated embodiment of FIG. 2B, the first, second, and third pumps 128A-128C pump the injection fluid through the internal annulus 130 and into the petroleum-bearing zone. In one or more embodiments, a different electrical, mechanical, or hydroelectrical mechanism is deployed to pump or to cause the injection fluid to flow into the injection zone. At block S310, the injection fluid is injected into a first portion of the formation that is along the injection zone of the borehole. In the embodiments of FIGS. 2A and 2B, water is injected into the first portion of the formation 112A. More particularly, water (or another type of fluid) is injected by a fluid injection device of the in-situ formation property measurement tool 120 into the first portion of the formation 112A. In some embodiments, the injection fluid is injected at a constant rate or at an approximate constant rate to reduce or eliminate damage to the first portion of the formation 112A. In one or more of such embodiments, the injection fluid is injected at a constant rate or at an approximate constant rate that is below a fracture pressure of the first portion of the formation 112A. In some embodiments, the injection fluid is analyzed before being injected into the first portion of the formation 112A. In one or more of such embodiments, sensors, such as sensors 126 and 127, determine one or more fluid properties of the injection fluid. In one or more of such embodiments, a sample of the injection fluid is obtained and analyzed at another location in the downhole (e.g., by another downhole device), or is transported to the surface and analyzed on the surface. In one or more of such embodiments, the rate at which the injection fluid is injected into the first portion of the formation 112A is based on the determined fluid properties of the injection fluid.

In some embodiments, the injection fluid is treated with an additive, such as an additive described herein, before it is injected into the first portion of the formation to facilitate the injection process. In one or more of such embodiments, the additive is added while the injection fluid is in the source zone. In one or more of such embodiments, the additive is added while the injection fluid is flowing through the internal annulus. In one or more of such embodiments, the additive is added after the injection fluid flows into the injection zone but before the injection fluid is injected into the first portion of the formation 112A. In some embodiments, properties of a mixture of the injection fluid and the additive are determined and the properties of the first portion of the formation 112A are determined based on the properties of the mixture of the injection fluid and the additive. In some embodiments, formation properties of the first portion of the formation 112A are determined before being injected with the injection fluid. In one or more of such embodiments, the mobility of the first portion of the formation 112A is tested in-situ. In one or more of such embodiments, a sample core of the first portion of the formation 112A is obtained, transported to a surface-based laboratory, and analyzed in the surface-based laboratory to determine the formation properties of the first portion of the formation 112A. In one or more of such embodiments, the injection fluid is then injected at a rate that is based on the determined formation properties (e.g., based on the mobility) of the first portion of the formation 112A.

At block S312, at least one formation property of the first portion of the formation 112A is determined based on an injection of the injection fluid into the first portion of the formation 112A. In the illustrated embodiments of FIGS. 2A and 2B, sensor 126 measures one or more fluid properties of the injection fluid (e.g., the flow rate of the injection fluid, the density of the injection fluid, the viscosity of the injection fluid, the pressure of the injection fluid, etc.) as the injection fluid flows through the internal annulus 130, as the injection fluid flows into the injection zone, and as the injection fluid is injected into the first portion of the formation 112A. In one or more embodiments, the formation properties (e.g., the relative permeability of the first portion of the formation 112A, the fluid injection potential of the first portion of the formation 112A, the wettability of the first portion of the formation 112A, etc.) are determined based on the measurements obtained by the sensor 126. In some embodiments, after the first portion of the formation 112A is injected with the injection fluid, petroleum or a mixture of petroleum and the injected fluid (mixture) flows out of the first portion of the formation 112A, the sensor 126 also measures one or more fluid properties of petroleum or the mixture flowing through the first portion of the formation 112A, flowing into the injection zone, and flowing through the internal annulus 130. In one or more of such embodiments, the formation properties of the first portion of the formation 112A are determined based on the measured fluid properties of petroleum or mixture.

In one or more embodiments, the in-situ formation property measurement tool 120 includes a memory and a processing unit that stores the measured data and determines fluid properties of the first portion of the formation 112A (or a different portion of the formation 112). In some embodiments, data indicative of the measurements are transmitted (e.g., via telemetry) to a surface-based electronic device, such as the controller 184 of FIGS. 1A and 1B to determine the formation properties of the first portion of the formation 112A. In some embodiments, blocks S304, S306, S308, S310, and S312 are performed repeatedly or are simultaneously performed to isolate additional zones, pump injection fluid from one zone into another zone, inject the injection fluid into another portion of the formation, and determine the formation properties of the other portion of the formation. In one or more of such embodiments, a third zone and a fourth zone are isolated. While the third zone and the fourth zone are isolated, another injection fluid (a second injection fluid) filled in the third zone is withdrawn and pumped into the fourth zone, where the second injection fluid is injected into another portion (second portion) of the formation. The formation properties of the second portion of the formation is then determined and analyzed.

Figure 4:
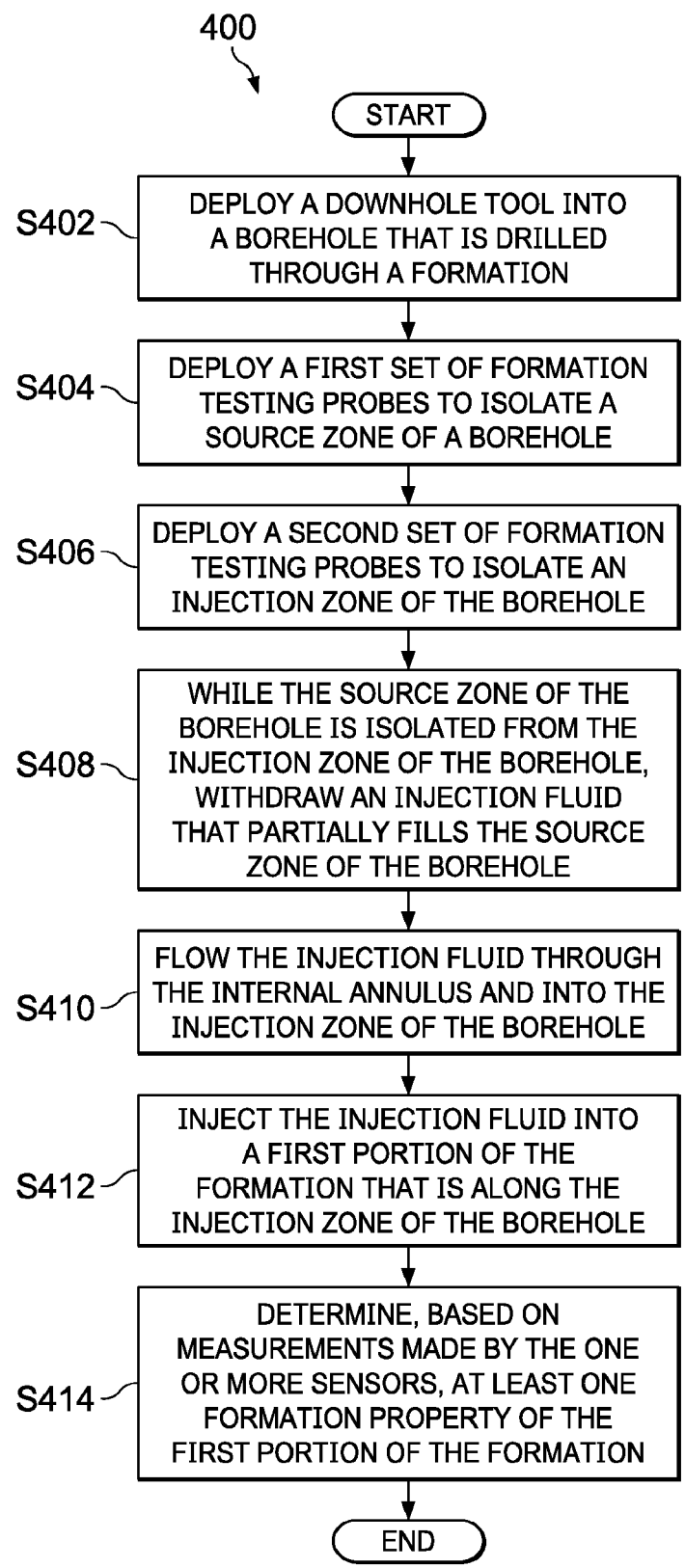
FIG. 4 is a flow chart of a process to operate any of the downhole tools of FIGS. 1A-1B, and 2A-2B to perform an in-situ determination of one or more formation properties of a downhole formation.

FIG. 4 is a flow chart of a process 400 to operate any of the downhole tools of FIGS. 1A-1B and 2A-2B to perform an in-situ determination of one or more formation properties of a downhole formation. Although the operations in the process 400 are shown in a particular sequence, certain operations may be performed in different sequences or at the same time where feasible.

At block S402, similar to block S302, a downhole tool is deployed into a borehole that is drilled through a formation. At block S404, a first set of formation testing probes of the downhole tool is deployed to isolate a source zone of the borehole. At block S406, a second set of formation testing probes of the downhole tool is deployed to isolate an injection zone of the borehole. In the embodiment of FIG. 2A, the first and second sets of formation testing probes 122A and 122C, and 122B and 122D, respectively, of the in-situ formation property measurement tool 120 are deployed to seal the water-bearing zone and the petroleum-bearing zone. In one or more embodiments, additional formation testing probes or additional sets of formation testing probes of the in-situ formation property measurement tool 120 are deployed to seal the water-bearing zone, the petroleum-bearing zone, and other zones.

At block S408, similar to block S306, while the source zone of the borehole is isolated from the injection zone of the borehole, an injection fluid that partially fills the source zone of the borehole is withdrawn. At block S410, similar to block S308, the injection fluid flows through the internal annulus and into the injection zone of the borehole. In the illustrated embodiment of FIG. 2B, the first, second, and third pumps 128A-128C pump the injection fluid through the internal annulus 130 and into the petroleum-bearing zone. At block S412, similar to block S310, the injection fluid is injected into a first portion of the formation that is along the injection zone of the borehole. At block S414, at least one formation property of the first portion of the formation is determined based on the measurements made by the at least one sensor of the downhole tool.

In some embodiments, the in-situ formation property measurement tool 120 includes one or more containers for storing a sample of the injection fluid (or another type of fluid). In some embodiments, the in-situ formation property measurement tool 120 includes a drill cutting tool operable of extracting a sample core from the formation. In one or more of the foregoing embodiments, the in-situ formation property measurement tool 120 is also operable of transporting the sample of the injection fluid and the sample core to another location downhole or to the surface for fluid analysis of the stored sample and the sample core.

The above-disclosed embodiments have been presented for purposes of illustration and to enable one of ordinary skill in the art to practice the disclosure, but the disclosure is not intended to be exhaustive or limited to the forms disclosed. Many insubstantial modifications and variations will be apparent to those of ordinary skill in the art without departing from the scope and spirit of the disclosure. For instance, although the flowcharts depict a serial process, some of the steps/processes may be performed in parallel or out of sequence, or combined into a single step/process. The scope of the claims is intended to broadly cover the disclosed embodiments and any such modification. Further, the following clauses represent additional embodiments of the disclosure and should be considered within the scope of the disclosure:

Clause 1, a method to perform an in-situ determination of a formation property of a downhole formation, the method comprising deploying a downhole tool into a borehole that is drilled through a formation; isolating a source zone of the borehole from an injection zone of the borehole; while the source zone of the borehole is isolated from the injection zone of the borehole: withdrawing an injection fluid that partially fills the source zone of the borehole; flowing the injection fluid into the injection zone of the borehole; injecting the injection fluid into a first portion of the formation that is along the injection zone of the borehole; and determining at least one formation property of the first portion of the formation based on an injection of the injection fluid into the first portion of the formation.

Clause 2, the method of clause 1, further comprising partially filling the source zone of the borehole with a formation fluid, wherein the injection fluid that partially fills the source zone of the borehole is at least one component of the formation fluid.

Clause 3, the method of clause 1 or 2, further comprising partially filling the source zone of the borehole with a drilling fluid, wherein the injection fluid that partially fills the source zone of the borehole is at least one component of the drilling fluid.

Clause 4, the method of clause 3, further comprising mixing the drilling fluid with an additive prior to injecting the drilling fluid into the first portion of the formation.

Clause 5, the method of clause 4, further comprising determining one or more properties of a mixture of the drilling fluid and the additive, wherein determining the at least one formation property of the first portion of the formation comprises determining the at least one formation property of the first portion of the formation based on the one or more properties of the mixture.

Clause 6, the method of any of clauses 1-5, further comprising partially filling the source zone of the borehole with petroleum of a hydrocarbon reservoir that is deposited in the formation, wherein the injection fluid that partially fills the source zone of the borehole is petroleum.

Clause 7, the method of any of clauses 1-6, wherein determining the at least one formation property of the first portion of the formation comprises determining a relative permeability of the first portion of the formation.

Clause 8, the method of any of clauses 1-7, wherein determining the at least one formation property of the first portion of the formation comprises determining a fluid injection potential of the first portion of the formation.

Clause 9, the method of any of clauses 1-8, further comprising determining a flow rate of the fluid flowing through the first portion of the formation, wherein determining the at least one property of the first portion of the formation is based on the flow rate of the fluid flowing through the first portion of the formation.

Clause 10, the method of any of clauses 1-9, further comprising obtaining a sample of the injection fluid; and determining one or more properties of the injection fluid, wherein determining the at least one property of the first portion of the formation comprises determining the at least one property based on one or more properties of the injection fluid.

Clause 11, the method of any of clauses 1-10, wherein injecting the injection fluid into the first portion of the formation comprises injecting the injection fluid at an approximate constant injection rate that is below a fracture pressure of the first portion of the formation.

Clause 12, the method of any of clauses 1-11, further comprising testing a mobility of the first portion of the formation prior to injecting the injection fluid into the first portion of the formation, wherein the injection fluid is injected at a rate that is based on the mobility of the first portion of the formation.

Clause 13, the method of any of clauses 1-12, further comprising after injecting the injection fluid into the first portion of the formation, determining at least one of a flow rate, a density, a viscosity, and a pressure of petroleum flowing out of the first portion of the formation into the injection zone of the borehole.

Clause 14, the method of any of clauses 1-13, further comprising isolating a third zone from a fourth zone; and while the third zone of the borehole is isolated from the fourth zone: withdrawing a second injection fluid that partially fills the third zone; flowing the second injection fluid into the fourth zone; injecting the second injection fluid into a second portion of the formation that is along the fourth zone; and determining at least one formation property of the second portion of the formation based on an injection of the second injection fluid into the second portion of the formation.

Clause 15, the method of any of clauses 1-14, further comprising measuring a pulse of the injection fluid while the injection fluid is injected into the first portion of the formation; and determining a pressure of the injection fluid based on the pulse of the injection fluid.

Clause 16, the method of clauses 1-15, further comprising determining one or more reservoir properties of a reservoir deposited proximate to the first portion of the formation based on the injection of the injection fluid into the first portion of the formation.

Clause 17, a method to operate a downhole tool to perform an in-situ determination of one or more formation properties of a downhole formation, comprising: deploying a downhole tool into a borehole that is drilled through a formation, the downhole tool comprising: a first set of formation testing probes; a second set of formation testing probes; an internal annulus; one or more fluid pumps; and one or more sensors; deploying the first set of formation testing probes to isolate a source zone of a borehole; deploying the second set of formation testing probes to isolate an injection zone of the borehole; while the source zone of the borehole is isolated from the injection zone of the borehole: withdrawing an injection fluid that partially fills the source zone of the borehole; flowing the injection fluid through the internal annulus and into the injection zone of the borehole; injecting the injection fluid into a first portion of the formation that is along the injection zone of the borehole; and determining, based on measurements made by the one or more sensors, at least one formation property of the first portion of the formation.

Clause 18, the method of clause 17, wherein the one or more fluid pumps comprise a first fluid pump and a second fluid pump, and wherein flowing the injection fluid further comprises: pumping, with the first fluid pump, the injection fluid from the source zone of the borehole into the internal annulus; and pumping, with the second fluid pump, the injection fluid from the internal annulus into the second pump.

Clause 19, an in-situ formation property measurement tool, comprising: a first set of formation testing probes for isolating a source zone of a borehole; a second set of formation testing probes for isolating an injection zone of the borehole; an internal annulus that forms a fluid flow path from a first portion of the tool that is deployed in the source zone of the borehole to a second portion of the tool that is deployed in the injection zone of the borehole; one or more fluid pumps for pumping an injection fluid that partially fills the source zone of the borehole into the injection zone of the borehole, wherein the injection fluid is injected into a first portion of the formation that is along the injection zone of the borehole; and one or more sensors operable to determine at least one formation property of the first portion of the formation.

Clause 20, the tool of clause 19, wherein the one or more fluid pumps comprises: a first pump operable to pump the injection fluid from the source zone of the borehole into the internal annulus; and a second pump operable to pump the injection fluid from the internal annulus to the injection zone of the borehole.

As used herein, the singular forms "a", "an" and "the" are intended to include the plural forms as well, unless the context clearly indicates otherwise. It will be further understood that the terms "comprise" and/or "comprising," when used in this specification and/or the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

The invention claimed is:

1. A method to perform an in-situ determination of a formation property of a downhole formation, the method comprising:
   deploying a downhole tool into a borehole that is drilled through a formation; wherein the downhole tool comprises a first and second set of formation testing probes;
   isolating a source zone of the borehole from an injection zone of the borehole with the first and second set of formation testing probes;
   while the source zone of the borehole is isolated from the injection zone of the borehole:
   withdrawing, at the source zone, an injection fluid that partially fills the source zone of the borehole;
   flowing the injection fluid from the source zone, through an internal annulus that fluidly connects the source zone and the injection zone, into the injection zone of the borehole;
   injecting the injection fluid into a first portion of the formation that is along the injection zone of the borehole; and
   while the injection fluid is being injected into the first portion of the formation, determining at least one formation property of the first portion of the formation based on the injection of the injection fluid into the first portion of the formation and one or more properties of the injection fluid.

2. The method of claim 1, further comprising partially filling the source zone of the borehole with a formation fluid, wherein the injection fluid that partially fills the source zone of the borehole is at least one component of the formation fluid.

3. The method of claim 1, further comprising partially filling the source zone of the borehole with a drilling fluid, wherein the injection fluid that partially fills the source zone of the borehole is at least one component of the drilling fluid.

4. The method of claim 3, further comprising mixing the drilling fluid with an additive prior to injecting the drilling fluid into the first portion of the formation.

5. The method of claim 4, further comprising determining one or more properties of a mixture of the drilling fluid and the additive, wherein determining the at least one formation property of the first portion of the formation comprises determining the at least one formation property of the first portion of the formation based on the one or more properties of the mixture.

6. The method of claim 1, further comprising partially filling the source zone of the borehole with petroleum of a hydrocarbon reservoir that is deposited in the formation, wherein the injection fluid that partially fills the source zone of the borehole is petroleum.

7. The method of claim 1, wherein determining the at least one formation property of the first portion of the formation comprises determining a relative permeability of the first portion of the formation.

8. The method of claim 1, wherein determining the at least one formation property of the first portion of the formation comprises determining a fluid injection potential of the first portion of the formation.

9. The method of claim 1, further comprising determining a flow rate of the injection fluid flowing through the first portion of the formation, wherein determining the at least one property of the first portion of the formation is based on the flow rate of the injection fluid flowing through the first portion of the formation.

10. The method of claim 1, further comprising:
obtaining a sample of the injection fluid; and
determining one or more properties of the sample,
wherein determining the at least one property of the first portion of the formation comprises determining the at least one property based on one or more properties of the sample.

11. The method of claim 1, wherein injecting the injection fluid into the first portion of the formation comprises injecting the injection fluid at an approximate constant injection rate that is below a fracture pressure of the first portion of the formation.

12. The method of claim 1, further comprising testing a mobility of the first portion of the formation prior to injecting the injection fluid into the first portion of the formation, wherein the injection fluid is injected at a rate that is based on the mobility of the first portion of the formation.

13. The method of claim 1, further comprising after injecting the injection fluid into the first portion of the formation, determining at least one of a flow rate, a density, a viscosity, and a pressure of petroleum flowing out of the first portion of the formation into the injection zone of the borehole.

14. The method of claim 1, further comprising:
isolating a third zone from a fourth zone; and
while the third zone of the borehole is isolated from the fourth zone:
withdrawing a second injection fluid that partially fills the third zone;
flowing the second injection fluid into the fourth zone;
injecting the second injection fluid into a second portion of the formation that is along the fourth zone; and
determining at least one formation property of the second portion of the formation based on an injection of the second injection fluid into the second portion of the formation.

15. The method of claim 1, further comprising:
measuring a pulse of the injection fluid while the injection fluid is injected into the first portion of the formation; and
determining a pressure of the injection fluid based on the pulse of the injection fluid.

16. The method of claim 1, further comprising determining one or more reservoir properties of a reservoir deposited proximate to the first portion of the formation based on the injection of the injection fluid into the first portion of the formation.

17. A method to operate a downhole tool to perform an in-situ determination of one or more formation properties of a downhole formation, comprising:
deploying a downhole tool into a borehole that is drilled through a formation, the downhole tool comprising:
a first set of formation testing probes;
a second set of formation testing probes;
an internal annulus;
one or more fluid pumps; and
one or more sensors;
deploying the first set of formation testing probes to isolate a source zone of a borehole;
deploying the second set of formation testing probes to isolate an injection zone of the borehole;
while the source zone of the borehole is isolated from the injection zone of the borehole:
withdrawing, at the source zone, an injection fluid that partially fills the source zone of the borehole;
flowing the injection fluid from the source zone, through the internal annulus, and into the injection zone of the borehole, wherein the internal annulus that fluidly connects the source zone and the injection zone;
injecting the injection fluid into a first portion of the formation that is along the injection zone of the borehole; and
determining, based on measurements made by the one or more sensors, at least one formation property of the first portion of the formation.

18. The method of claim 17, wherein the one or more fluid pumps comprise a first fluid pump and a second fluid pump, and wherein flowing the injection fluid further comprises:
pumping, with the first fluid pump, the injection fluid from the source zone of the borehole into the internal annulus; and
pumping, with the second fluid pump, the injection fluid from the internal annulus into the second pump.

19. An in-situ formation property measurement tool, comprising:
a first set of formation testing probes for isolating a source zone of a borehole;
a second set of formation testing probes for isolating an injection zone of the borehole;
an internal annulus that forms a fluid flow path from a first portion of the tool that is deployed in the source zone of the borehole to a second portion of the tool that is deployed in the injection zone of the borehole, wherein the internal annulus that fluidly connects the source zone and the injection zone;

one or more fluid pumps for pumping an injection fluid that partially fills the source zone of the borehole into the injection zone of the borehole, wherein the injection fluid is injected into a first portion of the formation that is along the injection zone of the borehole; and one or more sensors operable to determine at least one formation property of the first portion of the formation.

20. The tool of claim 19, wherein the one or more fluid pumps comprises:

a first pump operable to pump the injection fluid from the source zone of the borehole into the internal annulus; and a second pump operable to pump the injection fluid from the internal annulus to the injection zone of the borehole.

\* \* \* \* \*